United States Patent

Verbeek et al.

[11] Patent Number: 4,466,924
[45] Date of Patent: Aug. 21, 1984

[54] PLATINUM-DIAMINE COMPLEXES, A PROCESS FOR THE PREPARATION THEREOF, A PROCESS FOR THE PREPARATION OF A MEDICINE USING SUCH A PLATINUM-DIAMINE COMPLEX FOR THE TREATMENT OF MALIGNANT TUMORS IN MICE AS WELL AS A MEDICINE THUS FORMED

[75] Inventors: Francois Verbeek, Harmelen; Eric J. Bulten, Blaricum; Jan Berg, Nieuwegein, all of Netherlands

[73] Assignee: Nederlandse Centrale Organisatie voor Toegepast-Natuurwetenschappelijk Onderzoek, The Hague, Netherlands

[21] Appl. No.: 352,538

[22] Filed: Feb. 26, 1982

[30] Foreign Application Priority Data

Mar. 3, 1981 [NL] Netherlands .......................... 8101026

[51] Int. Cl.³ .............................................. C07F 15/00
[52] U.S. Cl. .................................. 260/429 R; 424/287
[58] Field of Search ..................................... 260/429 R

[56] References Cited

U.S. PATENT DOCUMENTS

| 4,119,653 | 10/1978 | Tobe et al. | 260/429 R |
| 4,119,654 | 10/1978 | Tobe et al. | 260/429 R |
| 4,137,248 | 1/1979 | Gale et al. | 260/429 R |
| 4,182,724 | 1/1980 | Tobe et al. | 260/429 R |
| 4,228,090 | 10/1980 | Hydes et al. | 260/429 R |
| 4,255,347 | 3/1981 | Kidani et al. | 260/429 R |

FOREIGN PATENT DOCUMENTS

| 0008936 | 3/1980 | European Pat. Off. |
| 7304880 | 10/1973 | Netherlands . |
| 7904740 | 1/1980 | Netherlands . |
| 7807334 | 1/1980 | Netherlands . |
| 8000032 | 8/1981 | Netherlands . |

OTHER PUBLICATIONS

B. Rosenberg and L. van Camp, Cancer Research 30, (1970), pp. 1799–1802.

(List continued on next page.)

[57] ABSTRACT

Platinum diamine complexes of the general formulae

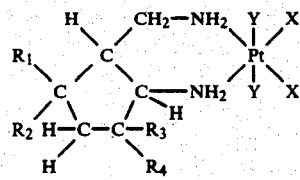

1.

AND

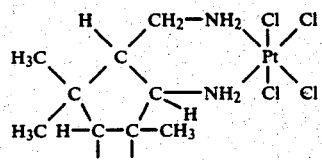

2.

wherein $R_1$ and $R_2$ independently from each other are a hydrogen atom or a substituted or unsubstituted alkyl, cyclo-alkyl, aryl or aralkyl group, while $R_1$ and $R_2$ may be together a substituted or unsubstituted cyclo-alkyl group, $R_3$ and $R_4$ independently of each other are a hydrogen atom or a substituted or unsubstituted alkyl, aryl or aralkyl group and X is a chlorine, bromine or iodine atom, a sulphate radical, a substituted or unsubstituted carboxylate rest like an acetate or substituted acetate radical, an oxalate, malonate, hydroxymalonate or otherwise substituted malonate group or a carboxylate group, the group Y, independently from X is a chlorine, bromine or iodine atom, a hydroxyl group, a nitrate group of a carboxylate group have been found to exhibit antitumor activity together with little or none kidney toxicity and are thus of interest as a medicament. Processes for the preparation of the platinum complexes are described and exemplified.

5 Claims, 7 Drawing Figures

1.
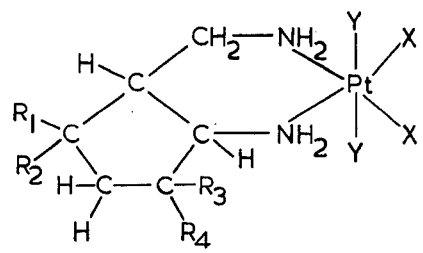
2.
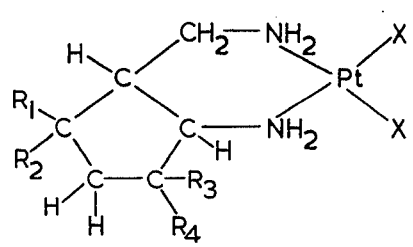
3.
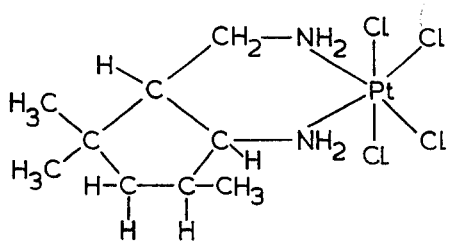
4.
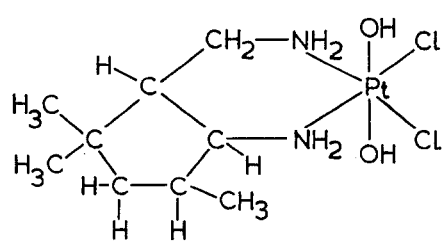
5.
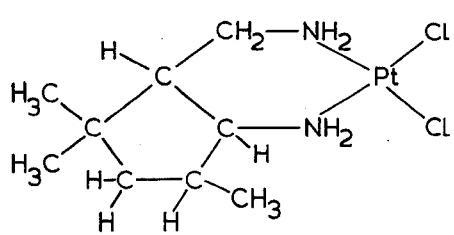
6.
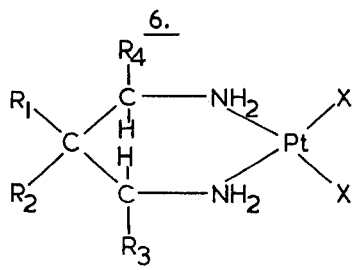
7.
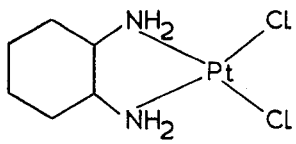

PLATINUM-DIAMINE COMPLEXES, A PROCESS FOR THE PREPARATION THEREOF, A PROCESS FOR THE PREPARATION OF A MEDICINE USING SUCH A PLATINUM-DIAMINE COMPLEX FOR THE TREATMENT OF MALIGNANT TUMORS IN MICE AS WELL AS A MEDICINE THUS FORMED

The invention relates to novel platinum-diamine complexes, to a process for the preparation thereof, to a process for the preparation of a medicine using such a platinum-diamine complex for the treatment of malignant tumors in mice, as well as to a medicine formed by application of this process.

From the literature it is known that platinum-diamine complexes are usable for the treatment of cancer. Vide for example the article by B. Rosenberg and L. van Camp, Cancer Research 30 (1970) 1799–1802 and the article by A. P. Zipp and S. G. Zipp, J.Chem. Ed., 54(12)(1977), page 739, which describes the use of cis-platinum-diaminechloride for the treatment of cancer. It is mentioned that these platinum compounds have a broad spectrum as antitumor agents, but also that they have important disadvantages, especially a toxicity to the kidneys. As a method for counteracting kidney toxicity a combination of the cis-platinum-diaminedichloride with another substance or with the use of large amounts of liquid or other techniques to bring about an adequate flow-through of the kidneys is proposed.

Further platinum-diamine complexes are described in J. Clinical Hematol; Oncol., 7 (1)(1977), pages 114–137. Wadley Medical Bulletin, vol. 7, No. 1, pages 231–241, Chem. and Eng. News, June 6, 1977, pages 29–30, and the article in Cancer Chemotherapy Reports Part 1, vol. 59, No. 3, May/June 1975, pages 629–641. From all these literature places it appears, that the complexes have a toxicity to kidneys.

Further literature being important with respect to platinum-diamine complexes are M. L. Tobe and A. R. Kohkhar, J.Clinical Hematol.Oncol. 7(1)(1977), the Dutch patent applications Nos. 7810431, 7903050 and 7903048 and J.Clinical Hematol.Oncol., 7(1)(1977), pages 231–241.

In the Dutch patent application No. 7904740 new platinum-diamine complexes are described, which are well suitable for the treatment of cancer and which exhibit little or none kidney toxicity. This relates to so called bidentate ligand complexes from bivalent platinum, characterized by formula 6 of the formula sheet, wherein the bidentate ligand is a substituted or unsubstituted propane diamine. Said compounds exhibit little or no kidney toxicity because of the nature of the substituents $R_1$, $R_2$, $R_3$ and $R_4$. Also the non-prepublished Dutch patent application No. 8000032 describes such complexes, which are well suitable for the treatment of cancer and have no kidney toxicity.

From the Dutch patent application Nos. 7304880, 7304881, 7304882 and 7703752 a large number of platinum-diamine complexes is known, among which the compound having the formula 7 of the formula sheet. In all compounds having a ring the nitrogen atoms are directly bonded to the ring. The compounds from the first mentioned three applications were compared with cis-platinum-diaminedichloride and appeared to be more active. About kidney toxicity in none of the applications anything is mentioned.

The present invention relates to new platinum-diamine complexes which are characterized by the formulae 1 and 2 of the formula sheet, wherein $R_1$ and $R_2$ independently from each other are a hydrogen atom or a substituted or unsubstituted alkyl, cycloalkyl, aryl or aralkyl group, while $R_1$ and $R_2$ together may be a substituted or unsubstituted cycloalkyl-group, $R_3$ and $R_4$ independently from each other are a hydrogen atom or a substituted or unsubstituted alkyl, aryl, or aralkyl group, and X is a chlorine, bromine or iodine atom, a sulphate radical, a substituted or unsubstituted carboxylate radical, like an acetate or substituted acetate radical, an oxalate, malonate, hydroxymalonate or otherwise substituted malonate group or a carboxyphthalate group, the group Y, independently from X, is a chlorine, bromine or iodine atom, a hydroxyl group, a nitrate group or a carboxylate group.

The compounds according to the invention which are preferred, are those having the formulae 3, 4 and 5 of the formula sheet.

The compounds exhibit a high antitumor activity against a large number of different types of malignant tumors in mice. like L 1210 lymphoide leukemia.

For information concerning this test procedure vide Instruction 14, Screening Data Summary Interpretation and Outline of Current Screen, Drug Evaluation Branch National Cancer Institute, Bethesda, Maryland 20014, 1977, T/C is the survival time for treated (T) versus non treated (C) mice; at a T/C>125 one speaks of a significant antitumor activity.

So for example the activity of the compounds having formula 5 against L 1210 lymphoid leukemia (T/C=214 at a dose of 120 mg/kg ip) is greater than that of cis-platinumdiaminedichloride (cis-PDD), which is practically used for the treatment of cancer (T/C=157–186 at a dose of 4–10 mg/kg ip). Among others also activity was observed against $B_{16}$-melano-carcinoma (T/C=155 at a dose of 4 mg/kg ip) and against Lewis lung carcinoma.

In contradiction to the cis-PDD mentioned before the present compounds do not exhibit detrimental effect on the activity of the kidneys (kidney-toxicity). This may be determined by determination of urea-nitrogen content in the blood, the so called BUN number (=percentages blood urean nitrogen). So for instance for ip administration of the compound having formula 5 in mice not any increase of the BUN number was observed for doses of 102, 136 and 181 mg/kg. antitumouractivity The preparation of the compounds according to the invention is further illustrated in the following examples. The compounds were prepared according to the methods of G. L. Johnson, Inorg. Synth.VIII, 242–244 (1966). and Basolo et al., J.Am.Chem.Soc. 72 (1950) 2433.

EXAMPLE I

Cis-dichloro-1-amino-2-aminomethyl-3,3,5-trimethyl-cyclopentane-platinum (II) having the formula 5 of the formule sheet 1-amino-2-aminomethyl-3,3,5-trimethylcyclopentane.2 HCl (2.2 g) and $K_2PtCl_4$ (4.15 g) were dissolved in 40 ml water. The mixture was heated at 95°–100° C. and a solution of 1 g NaOH in 20 ml water was added dropwise so quickly that the pH<6 was maintained. The formed precipitate was sucked, washed with water and dried. The product was taken up in 250–300 ml liquid $NH_3$ and filtrated. After evaporation of the $NH_3$ the product was washed with 2 n HCl, water and subsequently dried.

Yield: 3.4 g (85%)
Melting Point: 260° C.
Analysis (weight %)
Calculated: C 25.60 H 4.77 N 6.63 Cl 16.79
Found: 25.6 4.8 6.7 16.8
'H-NMR-spectrum in DMSO-d$_6$ (varian T-60) with respect to TMS:
$CH_3$ 0.93 ppm
$CH_2$ 1.2–2.4 ppm
$NH_2$ 4.90 ppm (broad) (3.97–6.13)
IR-spectrum in CsI

| cm$^{-1}$ | | cm$^{-1}$ | |
|---|---|---|---|
| 3420 | (w) | 1460 | (s) |
| 3250 | (m) | 1370 | (s) |
| 3200 | (m) | 1200 | (s) |
| 3130 | (m) | 1100 | (m) |
| 2960 | (m) | 990 | (w) |
| 2779 | (m) | 750 | (w) |
| 1570 | (s) | 320 | (s) (Pt-Cl) |

EXAMPLE II

Cis-tetrachloro-1-amino-2-aminomethyl-3,3,5-trimethylcyclopentaneplatinum (IV) having the formula 3 of the formula sheet 2 grams cis-dichloro-1-amino-2-aminomethyl-3,3,5-trimethylcyclopentane platinum (II) were suspended in 20 ml distilled water. Subsequently it was heated to 70° C., whereafter under stirring during 1 hour chlorine gas was introduced. The excess of chlorine gas was removed by passing air through the reaction mixture (temperature 70° C.).

The reaction mixture was cooled and the solid substance was filtrated, washed with water and dried under vacuum.

Weight of yellow solid substance: 1.8 g (77%)
Analysis: (weight %)
Calculated: C 21.92 H 4.09 N 5.68
Found: 22.5 4.0 5.7
'H-NMR spectrum in DMSO-d$_6$ (Varian T-60) with respect to TMS:
$CH_3$ 1.0 ppm
$CH_2$ 1.23–2.33 ppm
$NH_2$ 5.82–8.05 ppm (max. 6.98 ppm)
IR-spectrum (CsI-pill): Pt-Cl 340 cm$^{-1}$

EXAMPLE III

Cis-dichloro-trans-dihydroxy-1-amino-2-aminomethyl-3,3,5-trimethylcyclopentaneplatinum (IV) having the formula 4 of the formula sheet 2 grams of cis-dichloro-1-amino-2-aminomethyl-3,3,5-trimethylcyclopentaneplatinum (II) were suspended in 5 ml distilled water. To this 20 ml 30 percent hydrogen peroxide (±9 times excess) were added. The mixture is stirred during 0.5 hour at room temperature, thereafter during 1 hour at 70°–90° C. The suspension is cooled and the solid substance was filtrated, washed with water and dried under reduced pressure.

Weight of light yellow solid substance: 0.85 g (39%).
Analysis (weight %)
Calculated: C 23.69 H 4.86 N 6.14
Found: 23.8 4.7 5.9
IR-spectrum (CsI-pill): Pt-Cl 320 cm$^{-1}$; Pt-O 560 cm$^{-1}$.

We claim:
1. Platinum-diamine complexes having the formula:

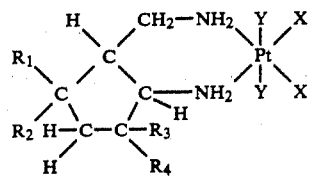

wherein $R_1$ and $R_2$ independently from each are selected from the group consisting of hydrogen, alkyl, cycloalkyl, aryl and aralkyl group, while $R_1$ and $R_2$, together may be a single cycloalkyl group, $R_3$ and $R_4$ independently of each other are selected from the group consisting of hydrogen, alkyl, aryl and aralkyl group, X is selected from the group consisting of a chlorine, bromine, iodine sulphate radical, acetate radical, oxalate, malonate, hydroxymalonate, and a carboxyphthalate group and Y independently from X is selected from the group consisting of chlorine, bromine, iodine, hydroxyl, nitrate and carboxylate.

2. Platinum-diamine complexes having the formula:

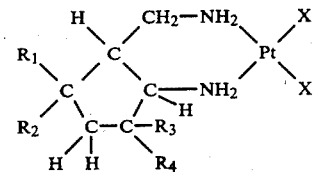

wherein $R_1$ and $R_2$ independently from each are selected from the group consisting of hydrogen, alkyl, cycloalkyl, aryl and aralkyl group, while $R_1$ and $R_2$, together may be a single cycloalkyl group, $R_3$ and $R_4$ independently of each other are selected from the group consisting of hydrogen, alkyl, aryl and aralkyl group, X is selected from the group consisting of a chlorine, bromine, iodine sulphate radical, acetate radical, oxalate, malonate, hydroxymalonate, and a carboxyphthalate group.

3. Platinum-diamine complex having the formula:

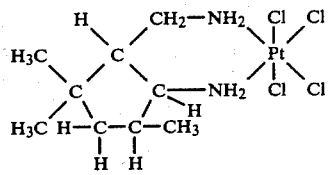

4. Platinum-diamine complex having the formula:

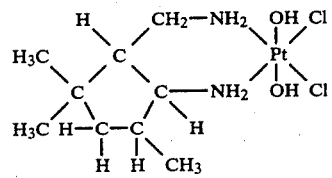

5. Platinum-diamine complex having the formula:

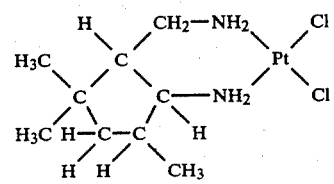

* * * * *